United States Patent
Zhang

(10) Patent No.: US 7,709,655 B2
(45) Date of Patent: May 4, 2010

(54) CLICKPHOSPHINES FOR TRANSITION METAL-CATALYZED REACTIONS

(75) Inventor: Xumu Zhang, Plainsboro, NJ (US)

(73) Assignee: The Penn State Research Foundation, University Park, PA (US)

( * ) Notice: Subject to any disclaimer, the term of this patent is extended or adjusted under 35 U.S.C. 154(b) by 752 days.

(21) Appl. No.: 11/445,464

(22) Filed: Jun. 2, 2006

(65) Prior Publication Data

US 2007/0088166 A1    Apr. 19, 2007

Related U.S. Application Data

(60) Provisional application No. 60/686,457, filed on Jun. 2, 2005.

(51) Int. Cl.
*C07D 257/00* (2006.01)
*C07D 403/00* (2006.01)
(52) U.S. Cl. .............................. 548/250; 568/8; 568/17
(58) Field of Classification Search ..................... 568/8, 568/17
See application file for complete search history.

(56) References Cited

U.S. PATENT DOCUMENTS 6,278,024 B1 *   8/2001   Zhang ........................ 568/17

OTHER PUBLICATIONS

Patani et al., Chem Rev, 1996, vol. 96 (8), especially p. 3147.*
Tanaka, et al. (J. Org. Chem., vol. 38(15), 1973, 2708-2712).*
Tanaka, et al. (Tetrahedron, vol. 29, 1973, 3271-3283)—cited on IDS.*
Tanaka, et al., J. Org. Chem., vol. 38(15), 1973, 2708-2712, especially p. 2710.*
Tanaka, et al., "Syntheses and Properties of H-1,2,3-Triazoles," Tetrahedron, 1973, pp. 3271-3283, vol. 29, Pergamon Press, Great Britain.
International Search Report and Written Opinion of the International Searching Authority issued in corresponding International Patent Application No. PCT/US06/21518, dated Sep. 15, 2006.

* cited by examiner

*Primary Examiner*—Susannah Chung
(74) *Attorney, Agent, or Firm*—McDermott Will & Emery LLP

(57) ABSTRACT

Phosphine triazole ligand compounds, prepared through click chemistry, complex with transition metals to form transition metal-phosphine triazole ligand complexes. These complexes are useful catalysts in coupling reactions such as Suzuki-Miyaura coupling, Stille coupling, Negishi coupling, Sonagashira coupling, carbon-heteroatom bond-forming reactions (C—O and C—N), alpha alkylation of carbonyls, Heck coupling reactions, and hydrogenation reactions.

18 Claims, No Drawings

CLICKPHOSPHINES FOR TRANSITION METAL-CATALYZED REACTIONS

CROSS-REFERENCE TO RELATED PATENT APPLICATIONS

This application claims the benefit of priority of Provisional Application No. 60/686,457, filed Jun. 2, 2005, which is incorporated herein by reference.

FIELD OF THE INVENTION

The present invention relates to phosphine ligand compounds prepared through click chemistry and related methods and their catalysts for applications in coupling and other catalytic reactions. More particularly, the present invention relates to transition metal complexes of these phosphine compounds. The transition metal complexes are useful in coupling reactions and other related reactions such as Suzuki-Miyaura coupling, Stille coupling, Negishi coupling, Sonagashira coupling, carbon-heteroatom bond-forming reactions (C—O and C—N), alpha alkylation of carbonyls, Heck coupling reactions, and hydrogenation reactions. Typical transition metal elements for coupling reactions are Pd and Ni as well as Mn, Fe, Rh and Cu. Hydrogenation catalysts include Rh, Ru, Ir and Pd complexes.

BACKGROUND

Transition metal catalyzed cross-coupling reactions have become a versatile tool in organic synthesis for the connections of two fragments via the formation of carbon-carbon bonds and carbon-heteroatom bonds. It is well-recognized that ligands employed in these processes have significant impact on the outcome of the reactions. Good ligands are those that cannot only stabilize and activate the transition metal center, but also direct the selectivity to the desired transformation. Therefore, designing ligands to impact bond formation is a challenging and desirable aspect in this area.

Transition metal-catalyzed coupling reactions involving C—C, C—N and C—O bonds are important in organic synthesis. [*Metal-Catalyzed Cross-coupling Reactions*; Diederich, F., Stang, P. J., Eds.; Wiley-VCH: New York, 1998]. A class of bulky, electron rich monophosphine ligands was developed by Buchwald [Old, D. W.; Wolfe, J. P.; Buchwald, S. L. *J Am. Chem. Soc.* 1998, 120, 9722-9723]. These ligands are illustrated below and can be used for C—C, C—N and C—O bond forming reactions [Wolfe, J. P.; Buchwald, S. L. *Angew. Chem., Int. Ed. Engl.* 1999, 38, 2413-2416. (c) Wolfe, J. P.; Singer, R. A.; Yang, B. H.; Buchwald, S. L. *J Am. Chem. Soc.* 1999, 121, 9550-9561. (d) Wolfe, J. P.; Tomori, H.; Sadighi, J. P.; Yin, J.; Buchwald, S. L. *J. Org. Chem.* 2000, 65, 1158-1174. (e) Aranyos, A.; Old, D. W.; Kiyomori, A.; Wolfe, J. P.; Sadighi, J. P.; Buchwald, S. L. *J. Am. Chem. Soc.* 1999, 121, 4369-4378].

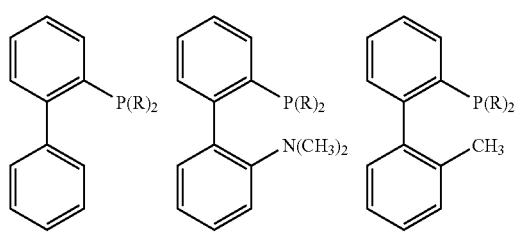

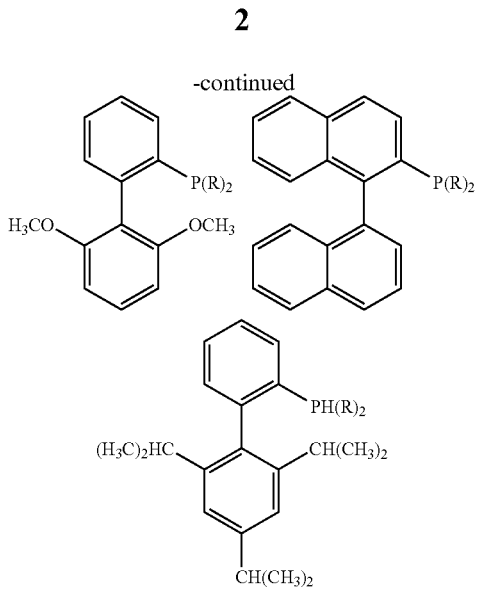

where R is a t-butyl group or a cyclohexyl group.

However, the synthesis of these ligands has been difficult and structural variations cannot be achieved easily. Recently, Beller reported a group of new monodentate phosphine ligands based on the 2-phosphino-N-arylpyrrol [Zarf, A.; Jackstell, R. Rataboul, F.; Riermeier, T.; Monsees, A.; Fuhrmann, C.; Shaikh, N.; Dingerdissen, U.; Beller, M. *Chem. Commun.* 2004, 38-39. (b) Rataboul, F.; Zarf, A.; Jackstell, R.; Harkal, S.; Riermeier, T.; Monsees, A.; Dingerdissen, U.; Beller, M. *Chem. Eur. J.* 2004, 10, 2983-2990]. Beller's ligands are illustrated below:

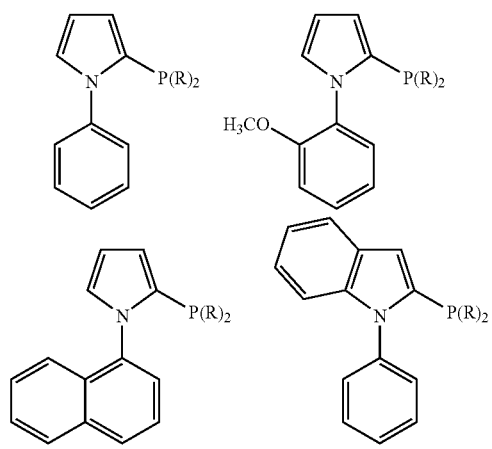

where R is the same as defined above. Comparable results have been achieved for coupling reactions.

Pd-catalyzed Suzuki-Miyaura coupling represents the most popular method for the preparation of biaryl compounds due to the advantages such as the wide functional group tolerance, stability and non-toxicity of the organoborane reagents. Some of the recent progress in this reaction has focused on the use of aryl chlorides as coupling partners in view of their attractive cost and readily available diversity. It is known that Pd complexes derived from sterically hindered and electron-rich phosphines are the most commonly effective catalysts for this transformation. Notably, using bulky trialkylphosphines such as t-(Bu)₃P, and dialkyl biphenylphosphines as illustrated below:

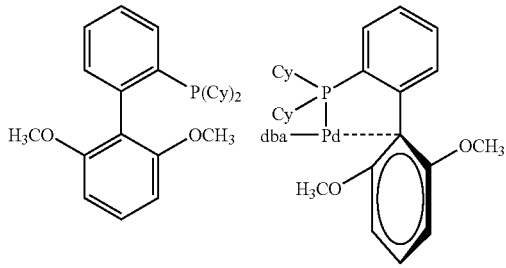

where Cy is a cyclohexyl group and dba is dibenzoylacetone. The compounds achieve very good yields in the Suzuki-Miyaura coupling involving various aryl chlorides as the coupling partners. Some other strategies such as using sterically hindered N-heterocyclic carbenes (NHCs) as ligands, and using palladacycles as the precatalysts, also lead to efficient catalytic systems for aryl chlorides coupling.

The development of metal-catalyzed coupling reactions depends on the innovation of structurally diverse ligands, which can be prepared efficiently. Click chemistry developed by Sharpless et al. is a rapid method for making structurally diverse motifs. The connectivity of making the motif is easy to be operated.

It is well-recognized that sterically bulky and electron-rich phosphines are preferred for challenge coupling partners since they can facilitate the formation of monoligated Pd species and lower the activation energy of the oxidative addition step. In addition to these effects, another important factor that might impact a high catalytic performance of biphenyl type ligands postulated by Buchwald et al.

SUMMARY OF THE INVENTION

The present invention is the synthesis of a set of novel triazole-based monophosphines which function as hemilabile ligands for cross-coupling reactions. These monophosphines are highly efficient for use in, for example, Suzuki-Miyaura coupling, Stille coupling, Negishi coupling, Sonagashira coupling, carbon-heteroatom bond-forming reactions (C—O and C—N), alpha alkylation of carbonyls, Heck coupling reactions, and hydrogenation reactions as well as amination reactions employing unactivated aryl chlorides.

DETAILED DESCRIPTION OF THE INVENTION

The present invention is directed to novel triazole-based monophosphines which function as ligands for use in metal-catalyzed coupling reactions. In particular, these monophosphines function as ligands that are useful for complexing with Pd, Ni, Mn, Fe, Rh, or Cu to catalyzed C—C, C—N, C—O bond coupling reactions as well as forming complexes with Rh, Ru, Ir and Pd for use in hydrogenation reactions. The mono-phosphines of the present invention are prepared using the "click chemistry" recently reported by Sharpless [Kolb, H.; Finn. M. G.; Sharpless, K. B. *Angew. Chem. Int. Ed.* 2001, 40, 2004-2021. Rostovtsev, V. V.; Green, L. G.; Fokin, V. V.; Sharpless, K. B. *Angew, Chem. Int. Ed.* 2002, 41, 2596-2599. Krasinski, A.; Fokin, V. V.; Sharpless, K. B. *Org. Lett.* 2004, 6, 3897-3899]. Collectively, the monophosphines or phosphine ligands of the present invention are herein also referred to as "clickphosphines".

A variety of phosphines can be made from click chemistry. The simplicity and versatility of the reactions in click chemistry allow the rapid structural change of phosphine ligands. However, prior to the present invention, no click chemistry method has been reported to introduce phosphine into a triazole ring.

By using phosphine chlorides as electrophiles, a variety of monophosphines can be prepared. Compared to the phosphine ligands developed by other groups, the ligand syntheses of the present invention are practical and structural variation is easy. Both azides and terminal alkynes are readily available in bulk quantities and their structure can be diversified conveniently.

Nitrogen atoms on the triazole rings bring unique electronic properties for the new ligands because of the hemilabile coordination of N to the Pd metallic center. It is believed that the chelating structure stabilizes the complex in a "resting state" where the coordination unsaturation is temporarily contained by the participation of the triazole ring.

Water soluble ligands are commonly used to produce hydrophilic catalysts that will be retained in the aqueous phase. An aqueous-biphasic catalyst has been used in the aqueous-phase hydroformylation of propylene. This invention is further directed to ligand synthesis by introducing water soluble groups into the ligands.

In accordance with this invention, the following triazole based monophosphine having structures (I) and (II) are prepared using click chemistry and are illustrated below:

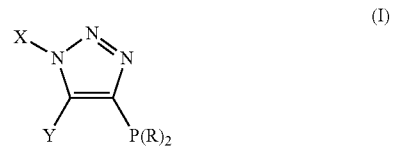
(I)

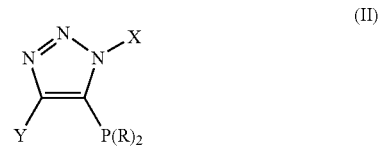
(II)

where X is hydrogen, alkyl, substituted alkyl, cycloalkyl, substituted cycloalkyl, aryl, substituted aryl, ferrocene, silane, hetereoaromatic group, or a substituted alkyl, substituted cylcoalkyl, or substituted aryl moiety having at least one stereogenic center; Y is hydrogen, alkyl, substituted alkyl, cycloalkyl, substituted cycloalkyl, aryl, substituted aryl, ferrocene, silane, hetereoaromatic group or a halide such as I, Br, or Cl; and R is an alkyl, substituted alkyl, cycloalkyl, substituted cycloalkyl, aryl, or substituted aryl group. In a particular embodiment, R is a t-butyl group (t-Bu), cyclohexyl group (Cy), adamantyl group (Ad), or phenyl group (Ph). The following are examples phosphine ligands having a substituted alkyl, substituted cycloalkyl, or substituted aryl moiety having a stereogenic center within the scope of this invention:

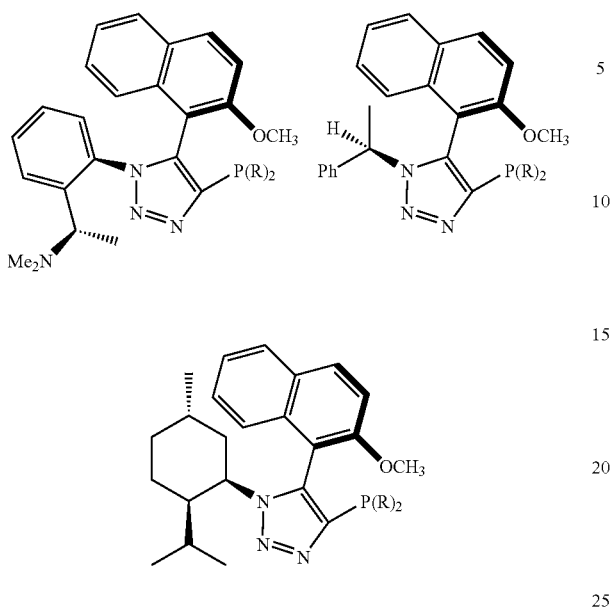

where R has the same meaning as set forth above. Asymmetric coupling reactions can then be realized in these systems.

The clickphosphines of structure (I) can be prepared by reacting Y—C≡C—MgCl or Y—C≡C—MgBr with X—N$_3$, where X and Y are defined as set forth above. The reaction scheme is set forth below in Reaction Scheme 1:

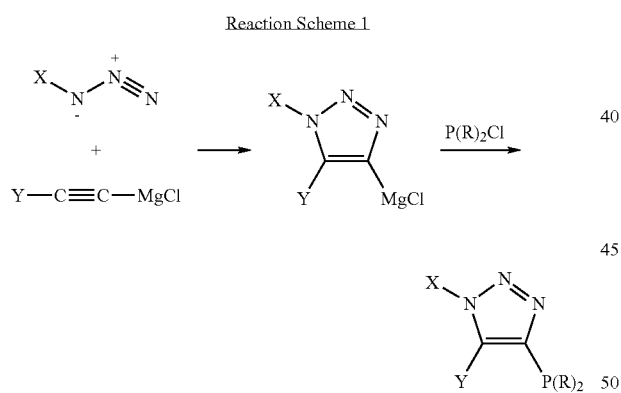

where R is the same as defined above. Examples of the clickphosphine ligands prepared accordance with Reaction Scheme 1 are set forth below as L1 to L12:

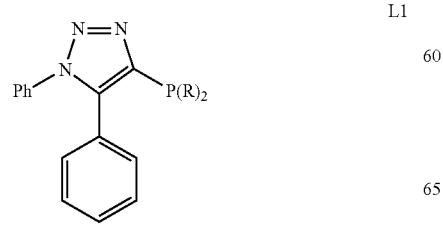

L1

-continued

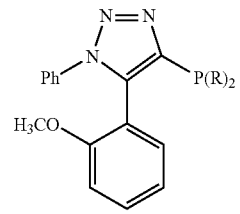

L2

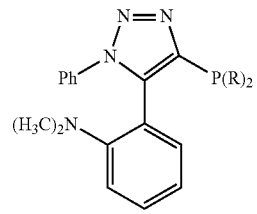

L3

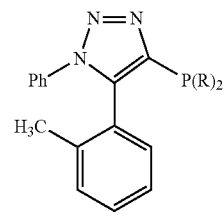

L4

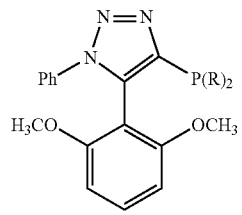

L5

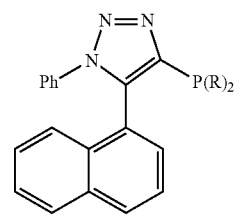

L6

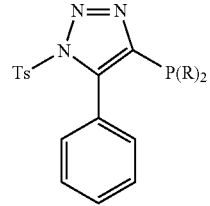

L7

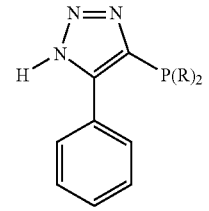

L8

-continued

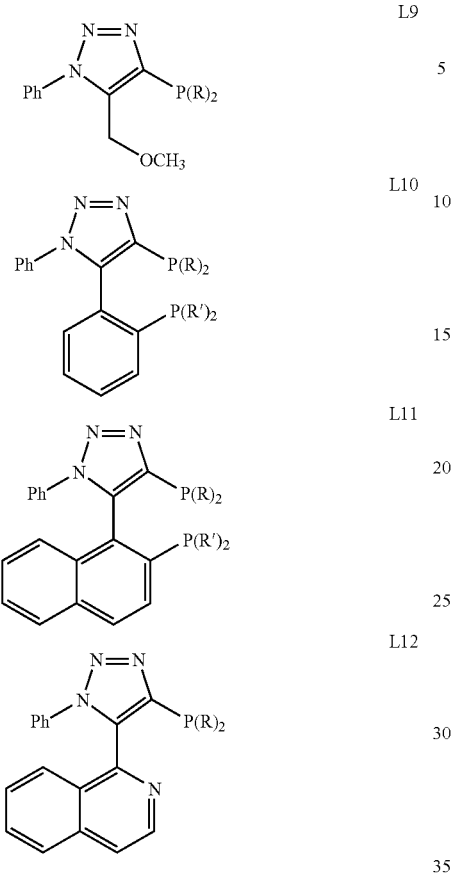

Importantly, when the X group has stereogenic centers, the formation of ligands can be influenced by the X group. Enantiomers of ligands can be generated. Therefore, chiral ligands can be prepared. Examples such ligands are illustrated above in paragraph [0015].

The clickphosphines having structure (II) can be prepared from a Cu-catalyzed method by reacting Y—C≡CH with X—N$_3$, where X and Y are defined as set forth above, in the presence of CuSO$_4$. The reaction scheme is set forth below in Reaction Scheme 2:

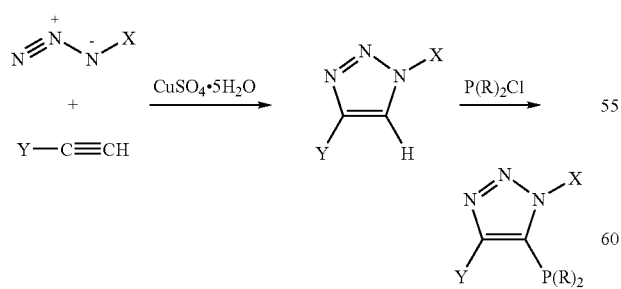

Examples of the clickphosphine ligands prepared in accordance with Reaction Scheme 2 are set forth below as L13 to L24:

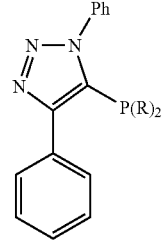

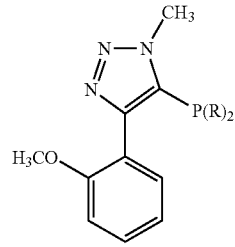

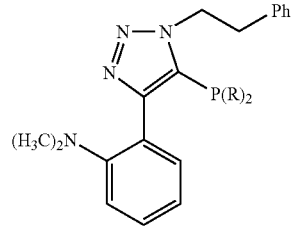

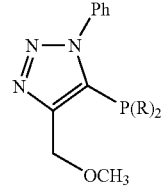

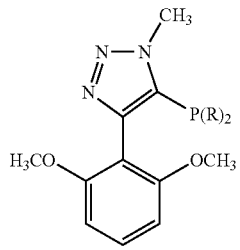

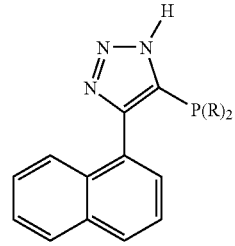

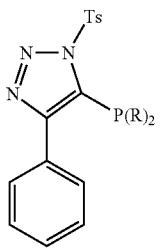

L19

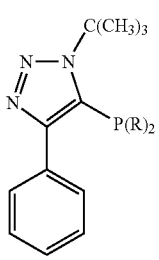

L20

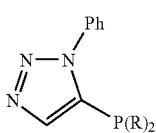

L21

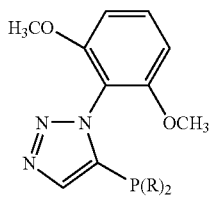

L22

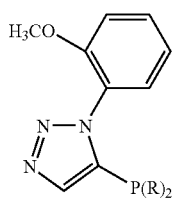

L23

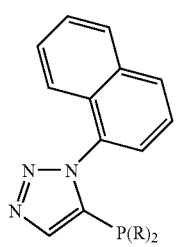

L24

Preparation of phosphine ligands having structures L21 to L24 requires the steps of forming a triazole, deprotonation, and then reaction with a phosphine chloride. While most of clickphosphine ligands having structures (I) and (II) are achiral ligands for coupling reactions, the biaryl type phosphine ligands such as those having structures L11 and L12 can be prepared in enantiomeric forms through oxidation of a bisphosphine oxide, resolution and reduction to bisphosphine. These biaryl-type clickphoshine ligands can also be used for asymmetric reaction such as hydrogenation and chiral C—C bond forming reactions. An example of a chiral ligand is set forth below as below as racemic bisphosphine having the following structure:

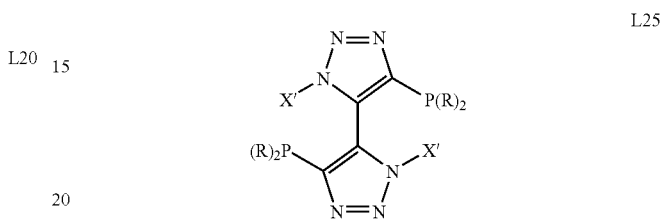

L25

This bisphosphine and its enantiomer can be prepared by oxidation of bisphosphine oxide, resolution and reduction to bisphosphine, where X' is an alkyl, substituted alkyl, cycloalkyl, substituted cycloalkyl, aryl, substituted aryl group, or a substituted alkyl, substituted cycloalkyl, or substituted aryl group having at least one sterogenic center; and R is an alkyl, substituted alkyl, cycloalkyl, substituted cycloalkyl, aryl, or substituted aryl group.

The phosphines of the present function as ligands which are useful for complexing with Pd, Ni, Mn, Fe, Rh, or Cu to catalyze C—C, C—N, C—O bond coupling reactions as well as forming complexes with Rh, Ru, Ir and Pd for use in hydrogenation reactions. They complex with transition metal compounds such as $PtCl_2$; $H_2PtCl_4$; $Pd(dba)_2$; $Pd_2(dba)_3$; $Pd(OAc)_2$; $PdCl_2(RCN)_2$; $(Pd(allyl)Cl)_2$; $(Rh(NBD)_2)Z$; $(Rh(NBD)Cl)_2$; $Rh(acac)(CO)_2$; $Rh(ethylene)_2(acac)$; $(Rh(ethylene)_2Cl)_2$; $RhCl(PPh_3)_3$; $Rh(CO)_2Cl_2$; $RuHZ(L)_2(diphosphine)$, $RuZ_2(L)_2(diphosphine)$, $Ru(arene)Z_2(diphosphine)$, $Ru(Ar)Z_2$; $Ru(RCOO)_2(diphosphine)$; $Ru(Ar)Z_2(PPh_3)_3$; $Ru(COD)(COT)$; $Ru(COD)(COT)Z$; $[RuZ_2(cymen)]_2$; $RuCl_2(COD)$; $(Ru(COD)_2)Z$; $RuZ_2(diphosphine)$; $Ru(Ar)Z_2(diphosphine)$, $Ru(ArH)Cl_2$; $Ru(COD)(methallyl)_2$; $CuZ(NCCH_3)_4$; $Cu(OTf)$; $Cu(OTf)_2$; $Cu(Ar)Z$; $CuZ$; $Ni(acac)_2$; $NiZ_2$; $(Ni(allyl)Z)_2$; $Ni(COD)_2$; $Fe(acac)_3$, $MnZ_2$ or $Mn(acac)_2$ where Z is a halide, R is an alkyl group, NBD is a diene, COD is cyclooctodiene, COT is cyclooctotriene, L is a ligand or solvent, Ar is an aryl group, acac is acetylacetate, and Tf is $CF_3SO_3$—. The catalyst and catalyst precursor can be $[Rh(COD)Cl]_2$, $[Rh(COD)_2]Q$ where Q is a halide, $BF_4$, $ClO_4$, $SbF_6$, $CF_3SO_3$, or $BAr_4$; $[Ir(COD)Cl]_2$, $[Ir(COD)_2]W$ where W is $BF_4$, $ClO_4$, $SbF_6$, or $CF_3SO_3$; chiral phosphines of the type illustrated as structures L11, L12 and L25 above; $Ru(RCOO)_2$diphosphine or $RuJ_2$(diphosphine) where J is Cl, Br or I; $Ru(methylallyl)_2$_(diphosphine); or other Ru catalysts with chiral phosphines. The complexes formed by the present invention further include coupling catalysts such as Pd $(II)A_2(L)_2$, Pd(0)L and $[Pd(I)A(L)]_2$ where A is Cl or Br, and L is ligand such as a triazole monophosphine ligand.

The phosphine ligands of the present invention can be used in any carbon-carbon coupling reaction or any carbon-heteroatom bond forming reaction. For example, the phosphine ligands are used in a Pd-catalyzed Suzuki-Miyaura coupling reaction as illustrated in Reaction Schemes 3 and 4 below:

Reaction Scheme 3

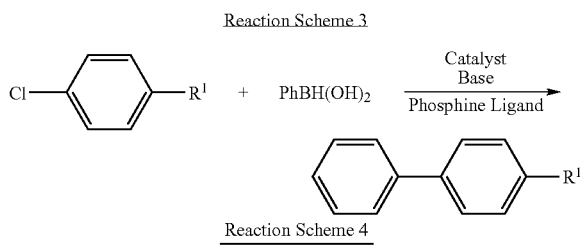

Reaction Scheme 4

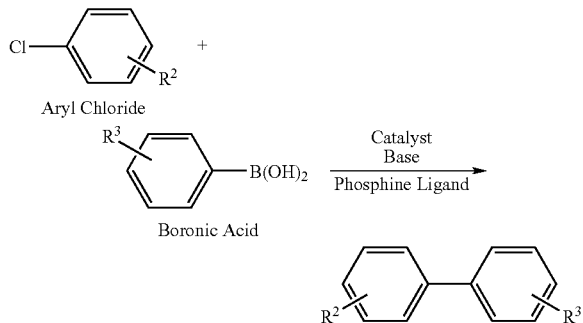

where $R^1$, $R^2$ and $R^3$ are independent and represent hydrogen, halide, alkyl, substituted alkyl, alkoxy, carboalkoxy, acetyl, alkylacetyl, alkene, substituted alkene, alkyne, substituted alkyne, cycloalkyl, substituted cycloalkyl, aryl, substituted aryl, heteroaromatic, substituted heteroaromatic, nitro or cyano group.

The phosphine ligands of the present invention can also be used in transition metal catalyzed amination reactions such as illustrated in Reaction Scheme 5 below:

Reaction Scheme 5

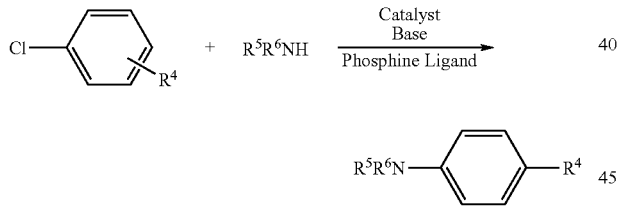

where $R^4$, $R^5$ and $R^6$ are independent and represent hydrogen, halide, alkyl, substituted alkyl, alkoxy, carboalkoxy, acetyl, alkylacetyl, alkene, substituted alkene, alkyne, substituted alkyne, cylcoalkyl, substituted cycloalkyl, aryl, substituted aryl, heteroaromatic, substituted heteroaromatic, nitro or cyano group; or $R^5$ and $R^6$ form a heterocyclic ring.

EXAMPLES

The following examples illustrate embodiments of the invention, but they are not to be considered as limiting the invention in any manner.

All reactions and manipulations in the examples which follow were performed in a nitrogen-filled glovebox or using standard Schlenk technique. THF and toluene were dried and distilled from sodium-benzophenone ketyl under nitrogen. Methylene chloride was distilled from $CaH_2$. Methanol was distilled from Mg under nitrogen. Column chromatography was performed using EM silica gel 60 (230~400 mesh). $^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard. MS spectra were recorded on a KRATOS mass spectrometer MS 9/50 for LR-EI and HR-EI. GC analysis was carried on Hewlett-Packard 6890 gas chromatography using chiral capillary columns. HPLC analysis was carried on WATERS 600 chromatography.

Example 1

Synthesis of Clickphosphines (L1a, L1b and L1c)

Clickphosphines L1a, L1b and L1c were prepared by reacting an phenyl azide with a phenyl alkyne Mg halide such as phenyl alkyne MgCl or phenyl alkyne MgBr and then with a substituted chlorophophine. The reaction scheme is illustrated below:

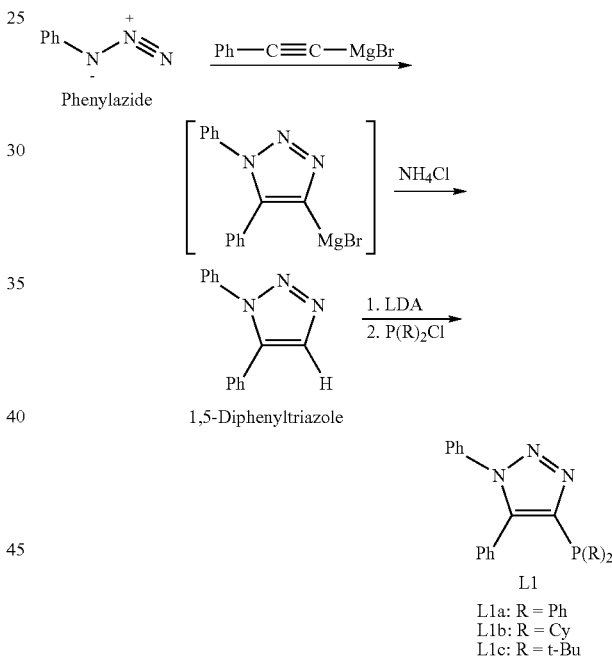

Following the first two steps reported by Sharpless et al. [Krasinski, A.; Fokin, V. V.; Sharpless, K. B. *Org. Lett*. 2004, 6, 1237], 1,5-diphenyltriazole was obtained in good yield by quenching, in situ, formed 4-bromomagnesium triazole intermediate with $NH_4Cl$. Treatment of the 1,5-diphenyltriazole with LDA (lithium di-isopropyl amide) followed by addition of chlorophosphine form a phosphine ligand having structure L1. Triazole phosphine compounds or phosphine ligands L1a, L1b and L1c were obtained in high yields. It is worthy of note that the synthesis could be shortened into a one pot operation with comparable crude yield of the desired product by directly quenching the intermediate 4 with chlorophosphine. The isolation of the 1,5-diphenyltriazole prior to adding the phosphino substituents is sorely due to the ease of purification of the final phosphine ligands, i.e. L1b and L1c.

Example 2

Preparation of the 1,5-Diphenyltriazole (1,5-Diphenyl-1H-[1,2,3]triazole)

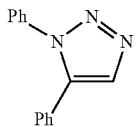

To a solution of EtMgBr in THF (1.0M, 11.9 mL) was added phenylacetylene (1.30 mL, 11.9 mmol) at room temperature. The reaction mixture was heated to 50° C. for 15 min. After cooling the mixture to room temperature, a solution of phenylazide (1.41 g, 11.9 mmol) in THF (4 mL) was added. The resulting solution was stirred at room temperature for 30 min, and then heated to 50° C. for 1 hour before quenching with saturated NH$_4$Cl (10 mL). The layers was separated, and the aqueous layer was extracted with CH$_2$Cl$_2$ (10 mL×3). The combined organic layers were dried over Na$_2$SO$_4$ and concentrated under reduced pressure. The residue was purified by flash column chromatography on silica gel to afford the 1,5-diphenyltriazole as a white solid (1.98 g, 75%). $^1$H NMR (CDCl$_3$, 300 MHz) δ 7.86 (s, 1H), 7.44-7.30 (m, 8H), 7.23-7.20 (m, 2H); $^{13}$C NMR (CDCl$_3$, 75 MHz) δ 137.6, 136.5, 133.4, 129.3, 129.2, 128.8, 128.5, 126.7, 125.1.

Example 3

Preparation of phosphine ligand (L1a)(4-Diphenylphosphanyl-1,5-diphenyl-1H-[1,2,3]triazole)

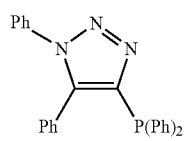

To a solution of 1,5-diphenyltriazole (0.260 g, 1.18 mmol) in THF (10 mL) at 0° C. was added LDA (1.24 mmol), which was prepared from diisopropylamine (0.174 mL, 1.24 mmol) and n-BuLi (1.24 mmol) at 0° C. The reaction mixture was stirred at 0° C. for 1.5 hours followed by addition of P(Ph)$_2$Cl (0.242 mL, 1.24 mmol). The resulting mixture was slowly warmed to room temperature and stirred for 1 hour. TLC showed the reaction was essentially complete. The organic solution was washed with brine (10 mL), dried over Na$_2$SO$_4$, and concentrated under reduced pressure. The residue was purified by flash column chromatography on silica gel (hexenes:EtOAc, 95:5) to obtain L1a as a white solid (0.43 g, 90%). $^1$H NMR (CDCl$_3$, 360 MHz) δ 7.73-7.69 (m, 4H), 7.44-7.36 (m, 14H), 7.26 (d, J=7.3 Hz, 2H); $^{13}$C NMR (CDCl$_3$, 90 MHz) δ 143.3 (d, J=39.5 Hz), 141.1 (d, J=14.2 Hz), 136.40, 136.38 (d, J=15.4 Hz), 133.8, 133.5, 130.1 (d, J=3.5 Hz), 129.2, 129.0, 128.8, 128.6, 128.35, 128.28, 128.2, 126.5, 124.8; $^{31}$P NMR (CDCl$_3$, 145 Hz) δ −35.85; HRMS (ESI+) calculated for C$_{26}$H$_{21}$N$_3$P (MH$^+$) 406.1475. found 406.1473.

Example 4

Preparation of Phosphine Ligand (L1b)(Dicyclohexylphosphanyl-1,5-diphenyl-1H-[1,2,3]triazole)

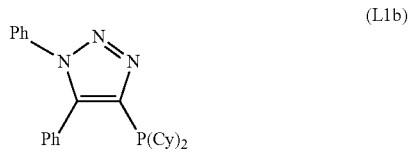

To a solution of 1,5-diphenyltriazole (0.500 g, 2.26 mmol) in THF (20 mL) at 0° C. was added LDA (2.26 mmol), which was prepared from diisopropylamine (0.317 mL, 2.26 mmol) and n-BuLi (2.26 mmol) at 0° C. The reaction mixture was stirred at 0° C. for 1.5 hours followed by addition of P(Cy)$_2$Cl (0.500 mL, 2.26 mmol). The resulting mixture was slowly warmed to room temperature and stirred for 4 hours. TLC showed the reaction was essentially complete. The organic solution was washed with brine (10 mL), dried over Na$_2$SO$_4$, and concentrated under reduced pressure. The residue was purified by flash column chromatography on silica gel under nitrogen (hexane:ether, 80:20) to obtain L1b as a white solid (0.88 g, 93%). $^1$H NMR (CD$_2$Cl$_2$, 360 MHz) δ 7.41-7.23 (m, 10H), 2.28-2.21 (m, 2H), 1.87-1.67 (m, 10H), 1.38-1.09 (m, 10H); $^{13}$C NMR (CDCl$_3$, 90 MHz) δ 144.7 (d, J=34.8 Hz), 141.2 (d, J=24.6 Hz), 137.2, 130.9 (d, J=2.9 Hz), 129.4, 129.3, 129.1, 128.6, 128.0, 125.3, 33.5 (d, J=8.4 Hz), 30.8 (d, J=16.3 Hz), 29.8 (d, J=7.5 Hz), 27.5 (d, J=18.5 Hz), 27.4 (d, J=1.6 Hz), 26.8; $^{31}$P NMR (CD$_2$Cl$_2$, 145 Hz) δ −27.76; HRMS (ESI+) calculated for C$_{26}$H$_{33}$N$_3$P (MH$^+$) 418.2419. found 418.2412.

Example 5

Preparation of Phosphine Ligand (L1c)(4-Di-tert-butylphosphanyl-1,5-diphenyl-1H-[1,2,3]triazole)

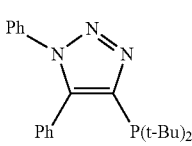

To a solution of 1,5-diphenyltriazole (0.520 g, 2.35 mmol) in THF (20 mL) at 0° C. was added LDA (2.35 mmol), which was prepared from diisopropylamine (0.329 mL, 2.35 mmol) and n-BuLi (2.35 mmol) at 0° C. The reaction mixture was stirred at 0° C. for 1.5 hours followed by addition of P(t-Bu)$_2$Cl (0.446 mL, 2.35 mmol). The resulting mixture was slowly warmed to room temperature and stirred overnight. TLC showed the reaction was essentially complete after 16 hours. The solvent was removed under vacuum. A degassed mixture of brine/H$_2$O (1:1) was added, and the resulting mixture was extracted with degassed ether (15 mL×3). The combined organic layers were dried over Na$_2$SO$_4$ and concentrated under vacuum. The residue was purified by flash column chromatography on silica gel under nitrogen (hexane:ether, 80:20) to obtain L1c as a sticky solid (0.78 g, 91%). $^1$H NMR (CD$_2$Cl$_2$, 360 MHz) δ 7.41-7.23 (m, 10H), 1.27 (d, J=12.1 Hz, 18H); $^{13}$C NMR (CDCl$^3$, 90 MHz) δ 145.2 (d, J=39.0 Hz), 142.2 (d, J=27.9 Hz), 137.2, 131.1 (d, J=2.5 Hz), 129.4, 129.3, 129.0, 128.6, 128.5, 125.2, 33.1 (d, J=17.0 Hz), 30.6 (d, J=14.4 Hz); $^{31}$P NMR (CD$_2$Cl$_2$, 145 Hz) δ 3.51; HRMS (ESI+) calculated for C$_{22}$H$_{29}$N$_3$P (MH$^+$) 366.2084. found 366.2099.

Example 6

General Procedure for Pd-Catalysed Suzuki-Miyaura Coupling Reaction

A Schlenk tube, which was flame-dried under vacuum and backfilled with nitrogen, was charged with boronic acid (1.5 mmol) and a base such as KF, CsF or K$_3$PO$_4$ (425 mg, 2 mmol). The flask was evacuated and backfilled with nitrogen three times. Toluene (3 mL), a stock solution of a phosphine ligand (2 mol %) in toluene, a stock solution of Pd(dba)$_2$ (1 mol %) in toluene, and aryl chloride (1.0 mmol) were subsequently added. The phosphine ligand can be, for example, L1a, L1b or L1c as described in the examples above, or L2 or L7 as set forth above, where R is t-butyl. The flask was sealed and the reaction mixture was heated to 80° C. with vigorous stirring for 12 hours. After cooling to room temperature, 10 mL of EtOAc was added and the mixture was washed with 10 mL of 1N NaOH (aq.) and 10 mL of brine. The organic layer was dried over Na$_2$SO$_4$ and concentrated under reduced pressure. The crude product was purified by flash column chromatography on silica gel. The yields of the coupling reaction using phosphine ligands described in this example coupled with catalyst Pd(dba)$_2$ are summarized forth in Table 1 below.

TABLE 1

Cl—C$_6$H$_4$—R$^1$ + PhBH(OH)$_2$ →[Pd(dba)$_2$, Base, Phosphine Ligand] Ph—C$_6$H$_4$—C$_6$H$_4$—R$^1$

| Sample | R$^1$ | Phosphine Ligand | Base | Yield |
|---|---|---|---|---|
| 1 | COCH$_3$ | Ph-triazole-P(Ph)$_2$ | K$_3$PO$_4$ | <10 |
| 2 | COCH$_3$ | Ph-triazole-P(Cy)$_2$ | K$_3$PO$_4$ | 85 |
| 3 | COCH$_3$ | Ph-triazole-P(t-Bu)$_2$ | K$_3$PO$_4$ | 99 |
| 4 | COCH$_3$ | Ph-triazole-P(t-Bu)$_2$ | KF | 99 |
| 5 | COCH$_3$ | Ph-triazole-P(t-Bu)$_2$ | CsF | 93 |
| 7 | CH$_3$ | Ph-triazole-P(t-Bu)$_2$ | KF | 86 |
| 8 | CH$_3$ | Ph-triazole-P(t-Bu)$_2$ | CsF | 57 |
| 9 | CH$_3$ | Ph-triazole-P(Ph)$_2$ | K$_3$PO$_4$ | <5 |
| 10 | CH$_3$ | Ph-triazole-P(Cy)$_2$ | K$_3$PO$_4$ | 70 |

TABLE 1-continued

Reaction scheme: 4-Cl-C6H4-R¹ + PhBH(OH)₂ → biphenyl-R¹ with Pd(dba)₂, Base, Phosphine Ligand

| Sample | R¹ | Phosphine Ligand | Base | Yield |
|---|---|---|---|---|
| 11 | CH₃ | Ph-N-N=N triazole with Ph and P(t-Bu)₂ | K₃PO₄ | 94 |
| 12 | CH₃ | Ph-N-N=N triazole with Np and P(t-Bu)₂ | K₃PO₄ | 88 |
| 13 | CH₃ | Ph-N-N=N triazole with Np and P(t-Bu)₂ | K₃PO₄ | 91 |
| 14 | CH₃ | Ph-N-N=N triazole with Np and P(Cy)₂ | K₃PO₄ | 88 |
| 15 | CH₃ | Ph-N-N=N triazole with (2-OCH₃-phenyl) and P(t-Bu)₂ | K₃PO₄ | 91 |
| 16 | CH₃ | Ph-N-N=N triazole with (2-OCH₃-phenyl) and P(Cy)₂ | K₃PO₄ | 20 |
| 17 | CH₃ | Ph-N-N=N triazole with (2-N(CH₃)₂-phenyl) and P(t-Bu)₂ | K₃PO₄ | 79 |
| 18 | CH₃ | Ph-N-N=N triazole with (2,6-di-OCH₃-phenyl) and P(t-Bu)₂ | K₃PO₄ | 95 |
| 19 | CH₃ | Ph-N-N=N triazole with (2,6-di-OCH₃-phenyl) and P(t-Bu)₂ | K₃PO₄ | 88 |

Example 7

Schlenk tube, which was flame-dried under vacuum and backfilled with charged with boronic acid (1.5 mmol) and a base such as $K_3PO_4$ (2 equiv.). The flask was evacuated and backfilled with nitrogen three times. Toluene (3 mL), a stock solution of a phosphine ligand (0.2 mol %) in toluene, a stock solution of Pd(dba)₂ (0.1 mol %) in toluene, and aryl chloride (1.0 mmol) were subsequently added. The phosphine ligand was L1c as described in Example 5 above. The flask was sealed and the reaction mixture was heated to 100° C. with vigorous stirring for 12 hours. After cooling to room temperature, 10 mL of EtOAc was added and the mixture was washed with 10 mL of 1N NaOH (aq.) and 10 mL of brine. The organic layer was dried over $Na_2SO_4$ and concentrated under reduced pressure. The crude product was purified by flash column chromatography on silica gel. The yields of the coupling reaction using phosphine ligand L1c coupled with catalyst Pd(dba)₂ are summarized forth in Table 2 below.

TABLE 2
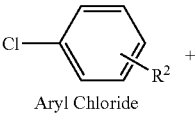
| Sample | Aryl Chloride | Boronic Acid | Product | Yield |
|---|---|---|---|---|
| 20 | 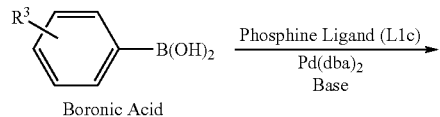 | PhB(OH)2 | 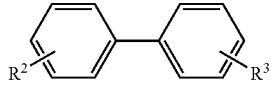 | 99 |
| 21 | 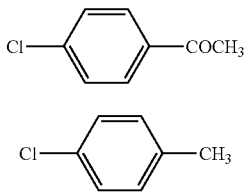 | PhB(OH)2 |  | 93[a] |
| 22 | 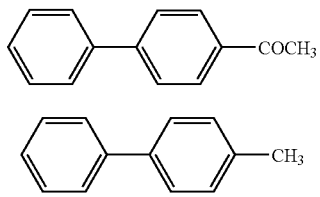 | PhB(OH)2 |  | 89 |
| 23 |  | PhB(OH)2 | 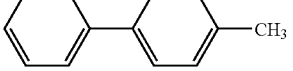 | 96 |
| 24 | 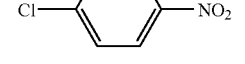 | PhB(OH)2 |  | 94 |
| 25 | 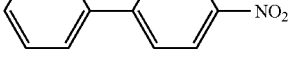 | PhB(OH)2 | 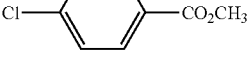 | 91 |
| 26 |  | PhB(OH)2 | 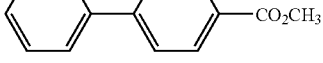 | 89 |
| 27 | 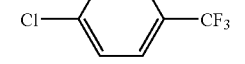 | PhB(OH)2 |  | 90 |
| 28 | 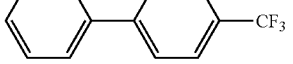 | PhB(OH)2 | 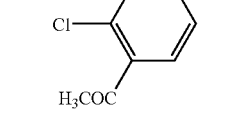 | 99 |
| 29 |  | PhB(OH)2 | 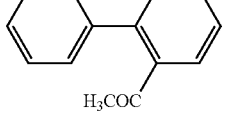 | 92 |

TABLE 2-continued
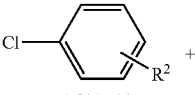
| Sample | Aryl Chloride | Boronic Acid | Product | Yield |
|---|---|---|---|---|
| 30 | 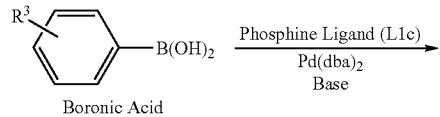 | PhB(OH)2 | 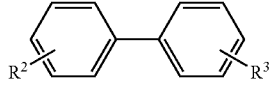 | 98 |
| 31 | 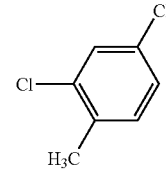 | PhB(OH)2 | 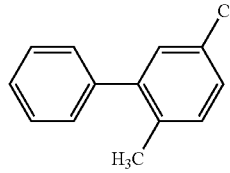 | 86 |
| 32 | 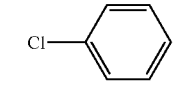 | 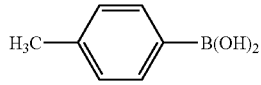 | 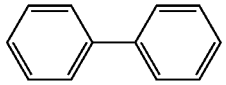 | 99 |
| 33 | 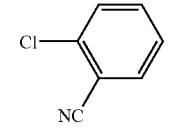 | 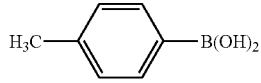 | 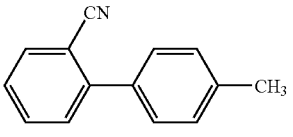 | 92 |
| 34 | 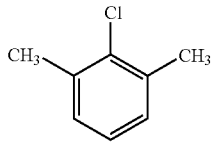 | 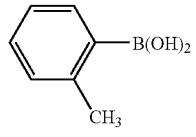 | 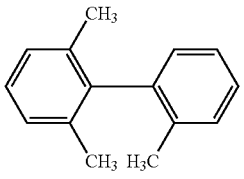 | 89[b] |
| 35 | 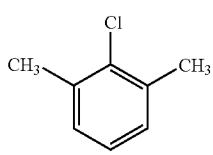 | 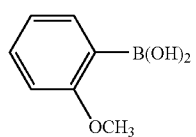 | 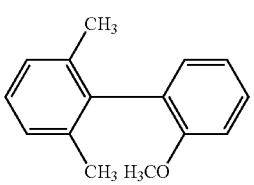 | 85[b] |
[a]For this sample, 0.01 mol % Pd(dba)$_2$ in toluene and 0.02 mol % of the phosphine ligand L1c in toluene were used.
[b]The reaction was carried out at 80° C.

The NMR properties of the coupling products of the Suzuki-Miyaura coupling reaction in Table 2 are set forth below.

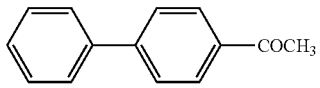

4-Acetylbiphenyl. $^1$H NMR (CDCl$_3$, 400 MHz) δ 8.04 (dd, J=1.6, 7.6 Hz, 2H), 7.69 (dd, J=1.6, 6.9 Hz, 2H), 7.65-7.62 (m, 2H), 7.50-7.41 (m, 3H), 2.64 (s, 3H); $^{13}$C NMR (CDCl$_3$, 90 MHz) δ 197.4, 145.4, 139.5, 135.6, 128.73, 128.67, 27.0, 126.9, 26.4.

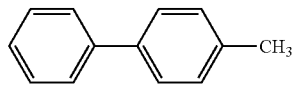

4-Methylbiphenyl. $^1$H NMR (CDCl$_3$, 400 MHz) δ 7.67-7.64 (m, 2H), 7.57 (dd, J=1.7, 6.4 Hz, 2H), 7.51-7.47 (m, 2H), 7.41-7.37 (m, 1H) 7.32 (d, J=7.9 Hz, 2H), 2.47 (s, 3H); $^{13}$C NMR (CDCl$_3$, 100 MHz) 67 141.1, 138.3, 137.0, 129.5, 128.7, 127.0, 126.9, 21.1.

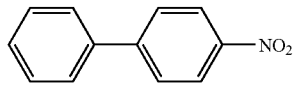

4-Nitrobiphenyl. $^1$H NMR (CDCl$_3$, 400 MHz) δ 8.30 (dt, J=2.5, 9.3 Hz, 2H), 7.74 (dt, J=2.0, 8.9 Hz, 2H), 7.65-7.62 (m, 2H), 7.53-7.45 (m, 3H); $^{13}$C NMR (CDCl$_3$, 100 MHz) δ 147.5, 147.0, 138.7, 129.1, 128.9, 127.7, 127.3, 124.0.

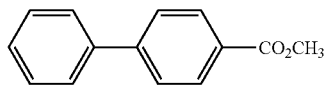

4-Carbomethoxybiphenyl. $^1$H NMR (CDCl$_3$, 400 MHz) δ 8.12 (dt, J=1.8, 8.5 Hz, 2H), 7.69-7.62 (m, 4H), 7.50-7.46 (m, 2H), 7.43-7.39 (m, 1H), 3.95 (s, 3H); $^{13}$C NMR (CDCl$_3$, 100 MHz) 6 166.9, 145.5, 139.9, 130.0, 128.9, 128.8, 128.1, 127.2, 127.0, 52.1.

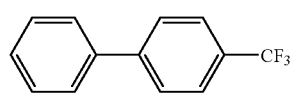

4-Trifluoromethylbiphenyl. $^1$H NMR (CDCl$_3$, 400 MHz) δ 7.72 (m, 4H), 7.64-7.62 (m, 2H), 7.52-7.43 (m, 3H); $^{13}$C NMR (CDCl$_3$, 100 MHz) δ 144.7, 139.8, 129.3 (q, J=32.1 Hz), 129.0, 128.2, 127.4, 127.3, 125.7 (q, J=3.7 Hz), 124.4 (q, J=272 Hz).

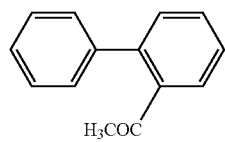

2-Acetylbiphenyl. $^1$H NMR (CDCl$_3$, 400 MHz) δ 7.58 (dd, J=1.2, 7.6 Hz, 1H), 7.53 (dt, J=1.4, 7.5 Hz, 1H), 7.47-7.35 (m, 7H), 2.03 (s, 3H); $^{13}$C NMR (CDCl$_3$, 100 MHz) δ 204.7, 140.8, 140.6, 140.4, 130.6, 130.1, 128.8, 128.6, 127.79, 127.77, 127.4, 30.3.

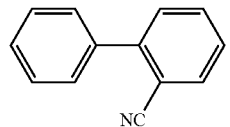

2-Cyanobiphenyl. $^1$H NMR (CDCl$_3$, 400 MHz) δ 7.77 (dd, J=1.1, 7.7 Hz, 1H), 7.65 (dt, J=1.3, 7.7 Hz, 1H), 7.59-7.57 (m, 2H), 7.53-7.44 (m, 5H); $^{13}$C NMR (CDCl$_3$, 100 MHz) δ 145.3, 138.0, 133.6, 132.7, 130.0, 128.63, 128.60, 127.4, 118.6, 111.1.

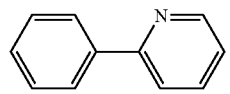

2-Phenyl-pyridine. $^1$H NMR (CDCl$_3$, 400 MHz) δ 8.71 (d, J=4.8 Hz, 1H), 8.01 (d, J=7.7 Hz, 2H), 7.72 (d, J=3.3 Hz, 2H), 7.50-7.40 (m, 3H), 7.21 (dd J=4.5, 8.6 Hz, 1H); $^{13}$C NMR (CDCl$_3$, 100 MHz) δ 157.3, 149.5, 139.3, 136.6, 128.8, 128.6, 126.8, 122.0, 120.4.

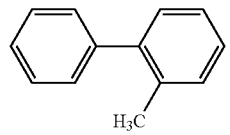

2-Methylbiphenyl. $^1$H NMR (CDCl$_3$, 400 MHz) δ 6 7.54-7.50 (m, 2H), 7.45-7.43 (m, 3H), 7.37-7.35 (m, 4H), 2.39 (s, 3H); 13C NMR (CDCl$_3$, 100 MHz) δ 141.94, 141.91, 135.3, 130.3, 129.8, 129.2, 128.0, 127.2, 126.7, 125.7, 20.4.

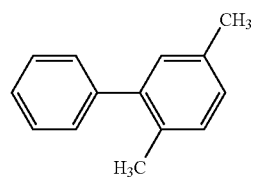

2,4-Dimethylbiphenyl. $^1$H NMR (CDCl$_3$, 400 MHz) δ 7.50-7.46 (m, 2H), 7.42-7.40 (m, 3H), 7.25 (d, J=8.2 Hz, 1H), 7.16 (d, J=3.8 Hz, 2H), 2.44 (s, 3H), 2.32 (s, 3H); $^{13}$C NMR (CDCl$_3$, 100 MHz) δ 142.1, 141.7, 135.1, 132.1, 130.5, 130.2, 129.1, 128.0, 127.9, 126.6, 20.9, 19.9.

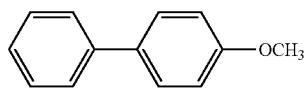

4-Methoxybiphenyl. $^1$H NMR (CDCl$_3$, 400 MHz) δ 7.61-7.56 (m, 4H), 7.47-7.43 (m, 2H), 7.36-7.32 (m, 1H), 7.01 (dt, J=2.2, 8.8 Hz, 1H), 3.88 (s, 3H); $^{13}$C NMR (CDCl$_3$, 100 MHz) δ 159.1, 140.8, 133.7, 128.7, 128.1, 126.7, 126.6, 114.1, 55.3.

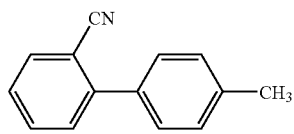

2-Cyano-4'-methylbiphenyl (81). $^1$H NMR (CDCl$_3$, 400 MHz) δ 7.76 (dd, J=0.9, 7.8 Hz, 1H), 7.63 (dt, J=1.3, 7.7 Hz, 1H), 7.51 (d, J=7.9 Hz, 1H), 7.49 (d, J=8.1 Hz, 2H), 7.42 (dt, J=1.1, 7.6 Hz, 1H), 7.32 (d, J=8.0 Hz, 2H), 2.43 (s, 3H); $^{13}$C NMR (CDCl$_3$, 100 MHz) δ 145.4, 138.5, 135.1, 133.6, 132.7, 129.9, 129.3, 128.5, 127.2, 118.8, 111.0, 21.1.

Example 8

A Schlenk tube, which was flame-dried under vaccum and backfilled with nitrogen, was charged with boronic acid (1.5 mmol) and a base such as K$_3$PO$_4$ (2 equiv.). The flask was evacuated and backfilled with nitrogen three times. Toluene (3 mL), a stock solution of a phosphine ligand (0.2 mol %) in toluene, a stock solution of Pd(dba)$_2$ (0.1 mol %) in toluene, and aryl chloride (1.0 mmol) were subsequently added. The phosphine ligand was L1c as described in Example 5 above. The flask was sealed and the reaction mixture was heated to 80° C. with vigorous stirring for 12 hours. After cooling to room temperature, 10 mL of EtOAc was added and the mixture was washed with 10 mL of 1N NaOH (aq.) and 10 mL of brine. The organic layer was dried over Na$_2$SO$_4$ and concentrated under reduced pressure. The crude product was purified by flash column chromatography on silica gel. The yields of the coupling reaction using phosphines described in this example coupled with catalyst Pd(dba)$_2$ are summarized forth in Table 3 below.

TABLE 3

| Sample | Aryl Chloride | Boronic Acid | Phosphine Ligand | Product | Yield |
|---|---|---|---|---|---|
| 36 | | | | | 89% |
| 37 | | | | | 85% |
| 38 | | | | | 96 |
| 39 | | | | | 95 |
| 40 | | | | | 12$^c$ |

TABLE 3-continued

| Sample | Aryl Chloride | Boronic Acid | Phosphine Ligand | Product | Yield |
|---|---|---|---|---|---|
| 41 | Cl, CH₃, CH₃ | B(OH)₂, OCH₃ | Ph-N-N=N, P(t-Bu)₂, H₃CO, OCH₃ | CH₃, CH₃, CH₃, H₃CO | 72ᶜ |
| 42 | Cl, CH₃, CH₃ | B(OH)₂, OCH₃ | Ph-N-N=N, P(Cy)₂, H₃CO, OCH₃ | CH₃, CH₃, CH₃, H₃CO | 57ᶜ |
| 43 | Cl, CH₃, CH₃ | B(OH)₂, CH₃ | Ph-N-N=N, Ph, P(t-Bu)₂ | CH₃, CH₃, CH₃, H₃C | 32ᶜ |
| 44 | Cl, CH₃, CH₃ | B(OH)₂, CH₃ | Ph-N-N=N, P(t-Bu)₂, H₃CO, OCH₃ | CH₃, CH₃, CH₃, H₃C | 90ᶜ |
| 45 | Cl, CH₃, CH₃ | B(OH)₂, CH₃ | Ph-N-N=N, P(Cy)₂, H₃CO, OCH₃ | CH₃, CH₃, CH₃, H₃C | 60ᶜ |

ᶜThe reaction was carried out at 120° C.

Example 9

General Procedure for Pd-Catalysed Amination Reactions

The phosphine ligand compounds of the present invention can be used in conjunction with transition metal catalysts employed in the animation of aryl chlorides. Pd-catalyzed amination of aryl halides has become a powerful method for the synthesis of aniline derivatives. Employing readily available aryl chlorides in this transformation has also become a focus and met with moderate success in recent years.

The procedure for the animation reaction using an unactivated aryl chloride in the presence of a transition metal catalyst and a phosphine ligand is as follows. A Schlenk tube, which was flame-dried under vaccum and backfilled with nitrogen, was charged with an amine (1.2 mmol) and a base such as KO(t-Bu) or NaO(t-Bu) (1.2 equiv.). The flask was evacuated and backfilled with nitrogen three times. Toluene (3 mL), a stock solution of a phosphine ligand (1.0-2.0 mol %) in toluene, a stock solution of a Pd catalyst (0.5-1.0 mol %) in toluene, and aryl chloride (1.0 mmol) were subsequently added. The flask was sealed and the reaction mixture was heated to 80° C. or 110° C. with vigorous stirring for 20-24 hours. After cooling to room temperature, 10 mL of EtOAc was added and the mixture was washed with 10 mL of 1N NaOH (aq.) and 10 mL of brine. The organic layer was dried over Na₂SO₄ and concentrated under reduced pressure. The crude product was purified by flash column chromatography on silica gel. The yields of the amination reaction using phosphine ligands described in this example coupled with Pd catalyst are summarized forth in Table 4 below.

TABLE 4

$$\text{Aryl-Cl} + R^5R^6NH \xrightarrow[\text{Base}]{\text{Catalyst, Phosphine Ligand}} R^5R^6N\text{-Aryl}$$

| Sample | Aryl Chloride | Amine | Ligand (mol %) | Temp | Reflux | Catalyst (mol %) | Base | Product | Yield |
|---|---|---|---|---|---|---|---|---|---|
| 46 | 4-Cl-C6H4-CH3 | PhNH2 | Ph-triazole-P(t-Bu)2 with o-OCH3-phenyl (1.0%) | 110° C. | 20 hr | Pd(dba)2 (0.5%) | NaO(t-Bu) | 4-CH3-C6H4-NH-Ph | 95% |
| 47 | 4-Cl-C6H4-CH3 | PhNH2 | Ph-triazole-P(Cy)2, Ph (1.0%) | 80° C. | 24 hr | Pd(dba)2 (0.5%) | NaO(t-Bu) | 4-CH3-C6H4-NH-Ph | 91% |
| 48 | 4-Cl-C6H4-CH3 | PhNH2 | Ph-triazole-P(t-Bu)2, Ph (1.0%) | 80° C. | 24 hr | Pd(dba)2 (0.5%) | KO(t-Bu) | 4-CH3-C6H4-NH-Ph | 94% |
| 49 | 4-Cl-C6H4-CH3 | PhNH2 | Ph-triazole-P(t-Bu)2, Ph (2.0%) | 110° C. | 24 hr | Pd(dba)2 (1.0%) | KO(t-Bu) | 4-CH3-C6H4-NH-Ph | 94% |

TABLE 4-continued

| Sample | Aryl Chloride | Amine | Ligand (mol %) | Temp | Reflux | Catalyst (mol %) | Base | Product | Yield |
|---|---|---|---|---|---|---|---|---|---|
| 50 | 4-Cl-C6H4-CH3 | PhNH2 | Ph-triazole-P(t-Bu)2 (2.0%) | 80° C. | 24 hr | Pd(dba)2 (1.0%) | KO(t-Bu) | 4-CH3-C6H4-NH-Ph | 92% |
| 51 | 4-Cl-C6H4-CH3 | PhNH2 | Ph-triazole-P(t-Bu)2 (2.0%) | 80° C. | 24 hr | Pd(dba)2 (1.0%) | KO(t-Bu) | 4-CH3-C6H4-NH-Ph | 87% |
| 52 | 4-Cl-C6H4-CH3 | PhNH2 | Ph-triazole-P(t-Bu)2 (2.0%) | 110° C. | 24 hr | Pd(dba)2 (1.0%) | NaO(t-Bu) | 4-CH3-C6H4-NH-Ph | 94% |
| 53 | 4-Cl-C6H4-CH3 | PhNH2 | Ph-triazole-P(t-Bu)2 (1.0%) | 80° C. | 24 hr | Pd(dba)2 (0.5%) | NaO(t-Bu) | 4-CH3-C6H4-NH-Ph | 88% |
| 54 | 4-Cl-C6H4-CH3 | PhNH2 | Ph-triazole-P(t-Bu)2 (1.0%) | 110° C. | 24 hr | Pd(dba)2 (0.5%) | NaO(t-Bu) | 4-CH3-C6H4-NH-Ph | 92% |

TABLE 4-continued

| Sample | Aryl Chloride | Amine | Ligand (mol %) | Temp | Reflux | Catalyst (mol %) | Base | Product | Yield |
|---|---|---|---|---|---|---|---|---|---|
| 55 | 4-chlorotoluene | aniline | 1-Ph-4-P(t-Bu)₂-5-Ph-triazole (1.0%) | 80° C. | 24 hr | Pd(dba)₂ (0.5%) | NaO(t-Bu) | 4-methyl-N-phenylaniline | 92% |
| 56 | 4-chlorotoluene | aniline | 1-Ph-4-P(Cy)₂-5-Ph-triazole (1.0%) | 110° C. | 24 hr | Pd(dba)₂ (0.5%) | NaO(t-Bu) | 4-methyl-N-phenylaniline | 91% |
| 57 | 4-chlorotoluene | aniline | 1-Ph-4-P(Cy)₂-5-(1-naphthyl)-triazole (1.0%) | 110° C. | 24 hr | Pd(dba)₂ (0.5%) | NaO(t-Bu) | 4-methyl-N-phenylaniline | 90% |
| 58 | 4-chlorotoluene | aniline | 1-Ph-4-P(t-Bu)₂-5-(1-naphthyl)-triazole (1.0%) | 110° C. | 24 hr | Pd(dba)₂ (0.5%) | NaO(t-Bu) | 4-methyl-N-phenylaniline | 91% |

TABLE 4-continued
Catalyst
Base
Phosphine Ligand
| Sample | Aryl Chloride | Amine | Ligand (mol %) | Temp | | Catalyst (mol %) | Base | Product | Yield |
|---|---|---|---|---|---|---|---|---|---|
| 59 |  |  |  (1.0%) | 110° C. | Reflux 24 hr | Pd(dba)₂ (0.5%) | NaO(t-Bu) | 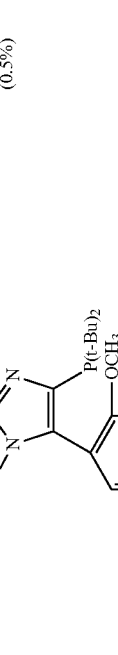 | 85% |
| 60 |  |  | 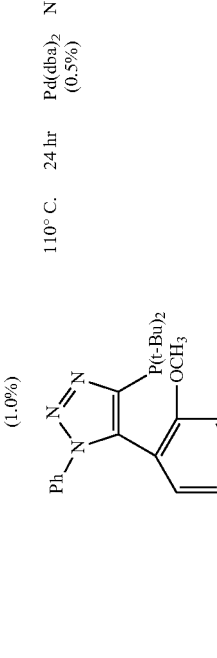 (1.0%) | 110° C. | 24 hr | Pd(dba)₂ (0.5%) | NaO(t-Bu) | 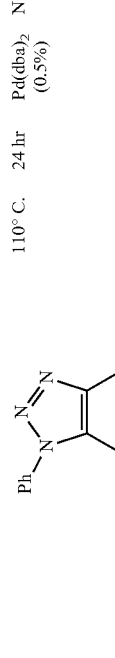 | 95% |
| 61 |  |  | 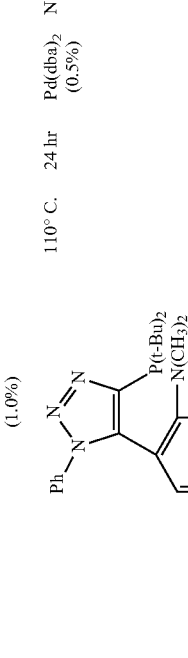 (1.0%) | 110° C. | 24 hr | Pd(dba)₂ (0.5%) | NaO(t-Bu) |  | 93% |

TABLE 4-continued
| Sample | Aryl Chloride | Amine | Ligand (mol %) | Temp | Reflux | Catalyst (mol %) | Base | Product | Yield |
|---|---|---|---|---|---|---|---|---|---|
| 62 | 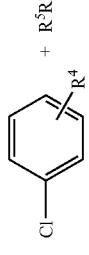 |  |  (1.0%) | 110° C. | 24 hr | Pd(dba)$_2$ (0.5%) | NaO(t-Bu) | 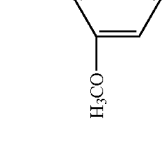 | 90% |
| 63 | 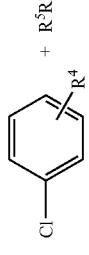 |  |  (1.0%) | 110° C. | 24 hr | Pd(dba)$_2$ (0.5%) | NaO(t-Bu) | 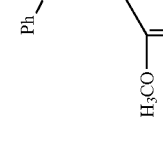 | 88% |
| 64 | 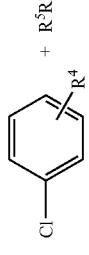 |  |  (1.0%) | 110° C. | 20 hr | Pd(dba)$_2$ (0.5%) | KO(t-Bu) | 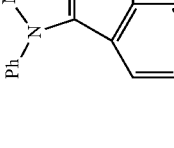 | 93% |

TABLE 4-continued

| Sample | Aryl Chloride | Amine | Ligand (mol %) | Temp | | Catalyst (mol %) | Base | Product | Yield |
|---|---|---|---|---|---|---|---|---|---|
| 65 | 4-chlorotoluene | Ph₂NH | Ph-triazole-P(t-Bu)₂/OCH₃ aryl (1.0%) | 110° C. | 20 hr | Pd(dba)₂ (0.5%) | NaO(t-Bu) | Ph₂N-C₆H₄-CH₃ | 94% |
| 66 | 4-chlorotoluene | Ph₂NH | Ph-triazole-P(t-Bu)₂/Ph (2.0%) | 80° C. | 24 hr | Pd(dba)₂ (1.0%) | KO(t-Bu) | Ph₂N-C₆H₄-CH₃ | 91% |
| 67 | 4-chlorotoluene | PhN(H)CH₃ | Ph-triazole-P(t-Bu)₂/OCH₃ aryl (1.0%) | 110° C. | 20 hr | Pd(dba)₂ (0.5%) | NaO(t-Bu) | Ph(CH₃)N-C₆H₄-CH₃ | 98% |
| 68 | 4-chlorotoluene | PhN(H)CH₃ | Ph-triazole-P(t-Bu)₂/Ph (1.0%) | 80° C. | 24 hr | Pd(dba)₂ (0.5%) | NaO(t-Bu) | Ph(CH₃)N-C₆H₄-CH₃ | 93% |

TABLE 4-continued

| Sample | Aryl Chloride | Amine | Ligand (mol %) | Temp | Reflux | Catalyst (mol %) | Base | Product | Yield |
|---|---|---|---|---|---|---|---|---|---|
| 69 | 4-chlorotoluene | morpholine | Ph-triazole-P(t-Bu)₂/OCH₃ (1.0%) | 110° C. | 20 hr | Pd(dba)₂ (0.5%) | NaO(t-Bu) | 4-(p-tolyl)morpholine | 97% |
| 70 | 4-chlorotoluene | 1-methylpiperazine | Ph-triazole-P(t-Bu)₂/OCH₃ (1.0%) | 110° C. | 20 hr | Pd(dba)₂ (0.5%) | NaO(t-Bu) | 1-methyl-4-(p-tolyl)piperazine | 88% |
| 71 | 4-chlorotoluene | dibenzylamine | Ph-triazole-P(t-Bu)₂/OCH₃ (1.0%) | 110° C. | 20 hr | Pd(dba)₂ (0.5%) | NaO(t-Bu) | N,N-dibenzyl-4-methylaniline | 78% |

TABLE 4-continued

Catalyst
Base
Phosphine Ligand

| Sample | Aryl Chloride | Amine | Ligand (mol %) | Temp | Reflux | Catalyst (mol %) | Base | Product | Yield |
|---|---|---|---|---|---|---|---|---|---|
| 72 | 4-chlorotoluene | butylamine | Ligand A (1.0%) | 110° C. | 20 hr | Pd(dba)₂ (0.5%) | NaO(t-Bu) | 4-methyl-N-butylaniline | 89%[d] |
| 73 | 2-chlorotoluene | aniline | Ligand A (1.0%) | 110° C. | 20 hr | Pd(dba)₂ (0.5%) | NaO(t-Bu) | 2-methyl-N-phenylaniline | 94% |
| 74 | 2-chlorotoluene | diphenylamine | Ligand A (1.0%) | 110° C. | 20 hr | Pd(dba)₂ (0.5%) | NaO(t-Bu) | 2-methyl-N,N-diphenylaniline | 96% |

TABLE 4-continued
| Sample | Aryl Chloride | Amine | Ligand (mol %) | Temp | Reflux | Catalyst (mol %) | Base | Product | Yield |
|---|---|---|---|---|---|---|---|---|---|
| 75 | 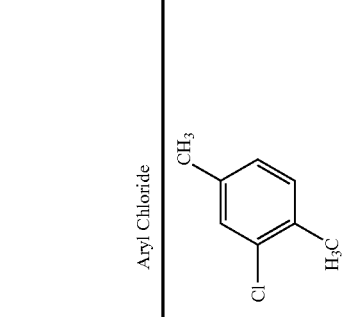 | 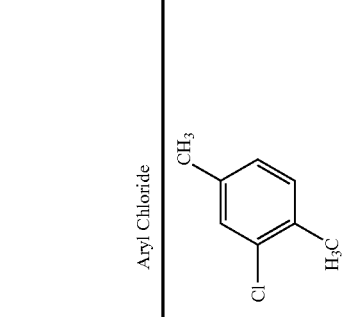 |  (1.0%) | 110° C. | 20 hr | Pd(dba)$_2$ (0.5%) | NaO(t-Bu) | 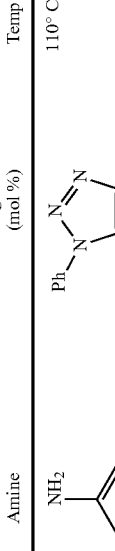 | 95% |
| 76 | 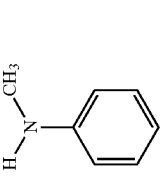 | 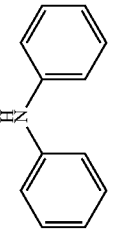 |  (1.0%) | 110° C. | 20 hr | Pd(dba)$_2$ (0.5%) | NaO(t-Bu) | 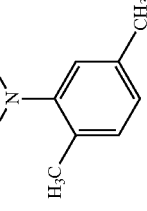 | 94% |
| 77 | 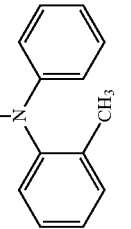 | 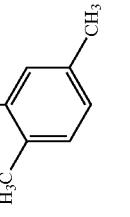 | (1.0%) | 80° C. | 24 hr | Pd(dba)$_2$ (0.5%) | NaO(t-Bu) | | 92% |
[d]In this sample, 5 equiv. of the amine was used.

These results indicate the potential applications of Pd/clickphosphine catalytic systems to a number of cross-coupling reactions.

In conclusion, the novel monophosphine ligand compounds of the present invention bear a triazole heterocycle in the backbone, which can act as hemilabile bidentate ligands for Pd-catalyzed crossing coupling reactions. The ligand synthesis is concise, efficient, and capable for further structural modification. Pd-ligand complexes derived from these monophosphine compounds provide highly active catalysts for Suzuki-Miyaura coupling. The monophosphines can be used in Pd-catalyzed amination reactions as well as other crossing coupling reactions.

The foregoing examples are considered as illustrative only of the principles of the invention. While the Suzuki-Miyaura coupling and amination reactions were given as examples in which the phosphine ligand compounds of the present invention can be used, they can be used with Stille coupling, Negishi coupling, Sonagashira coupling, carbon-heteroatom bond-forming reactions (C—O and C—N), alpha alkylation of carbonyls, Heck coupling reaction, and hydrogenation reaction to provide high yields of product. Further, since numerous modifications and changes will readily occur to those skilled in the art, it is not desired to limit the invention to the exact compositions and processes disclosed described herein. Accordingly, all suitable modifications and equivalence thereof may be resorted to, falling within the scope of the invention and embodiments thereof.

What is claimed is:

1. A phosphine compound selected from the group consisting of one of the following compounds:

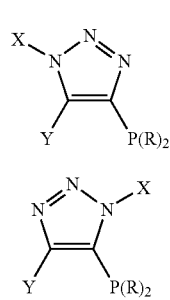

wherein where X is hydrogen, alkyl, substituted alkyl, cycloalkyl, substituted cycloalkyl, aryl, substituted aryl, ferrocene, silane, hetereoaromatic group, or a substituted alkyl, substituted cylcoalkyl, or substituted aryl moiety having at least one stereogenic center; Y is hydrogen, alkyl, substituted alkyl, cycloalkyl, substituted cycloalkyl, aryl, substituted aryl, ferrocene, silane, hetereoaromatic group or a halide such as I, Br, or Cl; and R is an alkyl, substituted alkyl, cycloalkyl, substituted cycloalkyl, aryl, or substituted aryl group.

2. The compound according to claim 1, wherein R is a t-butyl, cyclohexyl, adamantyl, or phenyl group.

3. The compound according to claim 1, wherein the phosphine compound comprises structure (I) and wherein X is a phenyl group; Y is a methoxymethylene, phenyl, substituted phenyl or 1-napthylene group; and R is a phenyl, cyclohexyl or t-butyl group.

4. The compound according to claim 3, wherein the substituted phenyl group is 2-methoxy phenyl, 2,6-dimethyl or 1-napthylene group.

5. The compound according to claim 4, wherein Y is a phenyl group and R is a cyclohexyl group.

6. The compound according to claim 4, wherein Y is a phenyl group and R is a t-butyl group.

7. The compound according to claim 4, wherein Y is a 1-napthyl group and R is a cyclohexyl group.

8. The compound according to claim 4, wherein Y is a 1-napthyl group and R is a t-butyl group.

9. The compound according to claim 4, wherein Y is a 2-methoxy phenyl group and R is a cyclohexyl group.

10. The compound according to claim 4, wherein Y is a 2-methoxy phenyl group and R is a t-butyl group.

11. The compound according to claim 4, wherein Y is a 2,6-dimethoxy phenyl group and R is a cyclohexyl group.

12. The compound according to claim 4, wherein Y is a 2,6-dimethoxy phenyl group and R is a t-butyl group.

13. The compound according to claim 4, wherein Y is a 2,-dimethylamine phenyl group and R is a t-butyl group.

14. The compound according to claim 1, wherein the phosphine compound comprises structure (II) and R is a phenyl, cyclohexyl or t-butyl group.

15. The compound according to claim 14, wherein X is hydrogen or a methyl, ethyl, t-butyl, phenyl, 2-methoxyphenyl, 2,6-dimethoxyphenyl, phenylethyl, tosyl or 1-naphthyl group and Y is hydrogen, methoxymethylene, phenyl, 2-methoxyphenyl, 2,6-dimethoxyphenyl, 2-dimethylaminophenyl or 1 naphthyl group.

16. The compound of claim 1, wherein the compound comprises one of the following structures:

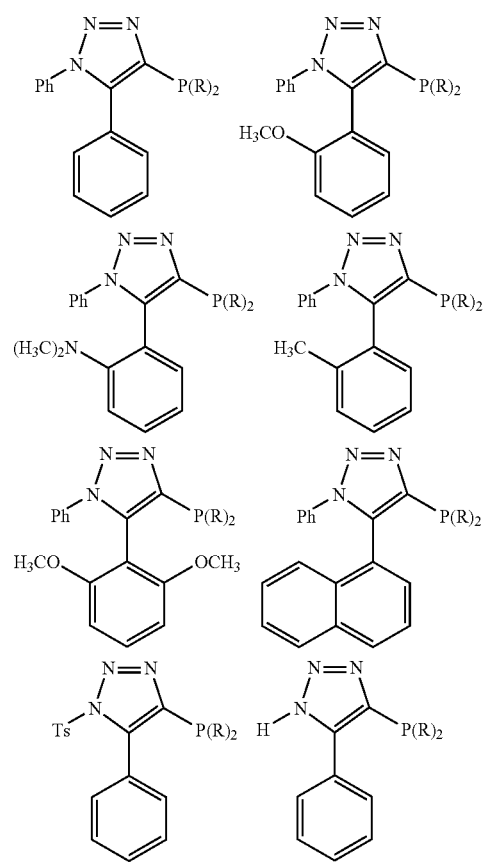

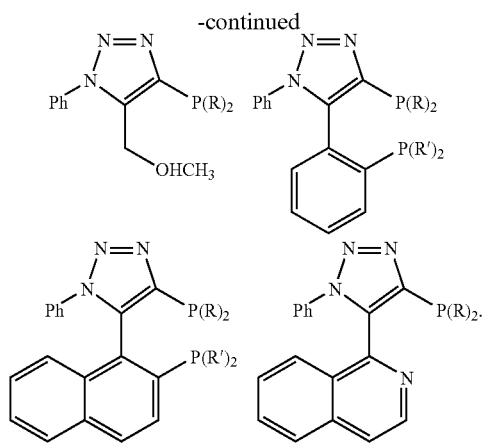

17. The compound of claim 1, wherein the compound comprises one of the following structures:

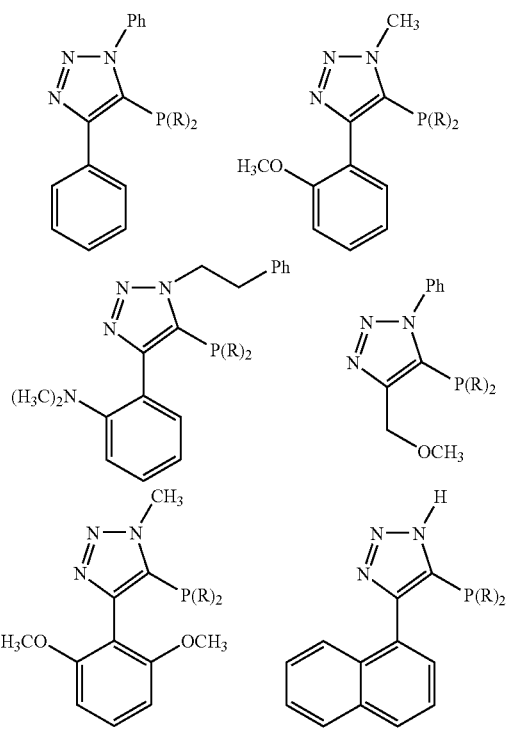

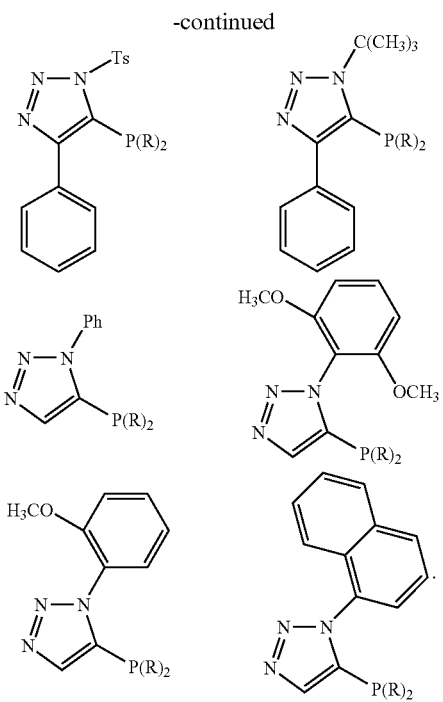

18. A racemic bisphosphine and its enantiomer having the following structural formula:

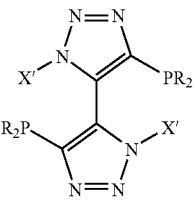

wherein X' is an alkyl, substituted alkyl, cycloalkyl, substituted cycloalkyl, aryl, substituted aryl, ferrocene, silane, hetereoaromatic group, or a substituted alkyl, substituted cylcoalkyl, or substituted aryl moiety having at least one stereogenic center; and R is an alkyl, substituted alkyl, cycloalkyl, substituted cycloalkyl, aryl, or substituted aryl group.

* * * * *

UNITED STATES PATENT AND TRADEMARK OFFICE
CERTIFICATE OF CORRECTION

| | |
|---|---|
| PATENT NO. | : 7,709,655 B2 |
| APPLICATION NO. | : 11/445464 |
| DATED | : May 4, 2010 |
| INVENTOR(S) | : Xumu Zhang |

Page 1 of 1

It is certified that error appears in the above-identified patent and that said Letters Patent is hereby corrected as shown below:

IN THE DESCRIPTION, COLUMN 1, line 3, below the title of the invention, insert:

--Government Interest in the Invention

This invention was made with government support under Grant No. GM058832, awarded by the National Institutes of Health. The Government has certain rights in the invention.--.

Signed and Sealed this
Twenty-fourth Day of May, 2011

David J. Kappos
*Director of the United States Patent and Trademark Office*